United States Patent
Boock

(10) Patent No.: US 6,312,421 B1
(45) Date of Patent: Nov. 6, 2001

(54) ANEURYSM EMBOLIZATION MATERIAL AND DEVICE

(75) Inventor: Robert Boock, Minnetonka, MN (US)

(73) Assignee: NeuroVasx, Inc., Maple Grove, MN (US)

( * ) Notice: Subject to any disclaimer, the term of this patent is extended or adjusted under 35 U.S.C. 154(b) by 0 days.

(21) Appl. No.: 09/360,027

(22) Filed: Jul. 23, 1999

(51) Int. Cl.⁷ .................. A61M 31/00; A61M 29/00; A61F 2/06
(52) U.S. Cl. .................. 604/509; 606/194; 623/1.42
(58) Field of Search .................. 604/500, 502, 604/509, 510, 508; 606/167, 170, 191, 192, 194; 623/1.12, 1.1, 1.2, 1.42, 11.11; 128/898

(56) References Cited

U.S. PATENT DOCUMENTS

| | | | |
|---|---|---|---|
| 4,735,201 | 4/1988 | O'Reilly | 128/303.1 |
| 5,122,136 | 6/1992 | Guglielmi et al. | 606/32 |
| 5,154,179 | 10/1992 | Ratner | 128/653.4 |
| 5,308,889 | 5/1994 | Rhee et al. | 523/113 |
| 5,354,295 | 10/1994 | Guglielmi et al. | 606/32 |
| 5,405,379 | 4/1995 | Lane | 623/1 |
| 5,538,008 * | 7/1996 | Crowe | 128/751 |
| 5,720,776 | 2/1998 | Chuter et al. | 623/1 |
| 5,769,882 | 7/1998 | Fogarty et al. | 623/1 |
| 5,817,017 | 10/1998 | Young et al. | 600/433 |
| 5,823,198 | 10/1998 | Jones et al. | 128/899 |
| 5,843,158 | 12/1998 | Lenker et al. | 623/1 |
| 5,911,731 * | 6/1999 | Pham et al. | 606/191 |
| 5,925,074 | 7/1999 | Gingras et al. | 623/1 |
| 6,015,424 | 1/2000 | Rosenbluth et al. | |
| 6,113,629 * | 9/2000 | Ken | 623/1.1 |
| 6,165,193 * | 12/2000 | Greene, Jr. et al. | 606/191 |

* cited by examiner

Primary Examiner—Richard K. Seidel
Assistant Examiner—Michael J Hayes
(74) Attorney, Agent, or Firm—Schwegman, Lundberg, Woessner & Kluth, P.A.

(57) ABSTRACT

The present invention includes a method for treating an aneurysm. The method includes providing a biocompatible polymeric string and transporting the string to an aneurysm. The aneurysm is filled with the string. The string is cut when the aneurysm is substantially filled.

17 Claims, 2 Drawing Sheets

ANEURYSM EMBOLIZATION MATERIAL AND DEVICE

BACKGROUND OF THE INVENTION

The present invention relates to an aneurysm embolization material and to a method for repairing an aneurysm.

An aneurysm is a balloon-like swelling in a wall of a blood vessel. An aneurysm results in weakness of the vessel wall in which it occurs. This weakness predisposes the vessel to tear or rupture with potentially catastrophic consequences for any individual having the aneurysm. Vascular aneurysms are a result of an abnormal dilation of a blood vessel, usually resulting from disease and/or genetic predisposition which can weaken the arterial wall and allow it to expand. Aneurysm sites tend to be areas of mechanical stress concentration so that fluid flow seems to be the most likely initiating cause for the formation of these aneurysms.

Aneurysm in a cerebral circulation tend to occur in an anterior communicating artery, posterior communicating artery, and a middle cerebral artery. The majority of these aneurysms arise from either curvature in the vessels or at bifurcations of these vessels. The majority of cerebral aneurysms occur in women. Cerebral aneurysms are most often diagnosed by the rupture and subarachnoid bleeding of the aneurysm.

Cerebral aneurysms are most commonly treated in open surgical procedures where the diseased vessel segment is clipped across the base of the aneurysm. While considered to be an effective surgical technique, particularly considering an alternative which may be a ruptured or re-bleed of a cerebral aneurysm, conventional neurosurgery suffers from a number of disadvantages. The surgical procedure is complex and requires experienced surgeons and well-equipped surgical facilities. Surgical cerebral aneurysm repair has a relatively high mortality and morbidity rate of about 2% to 10%.

Current treatment options for cerebral aneurysm fall into two categories, surgical and interventional. The surgical option has been the long held standard of care for the treatment of aneurysms. Surgical treatment involves a long, delicate operative procedure that has a significant risk and a long period of postoperative rehabilitation and critical care. Successful surgery allows for an endothehal cell to endothelial cell closure of the aneurysm and therefore a cure for the disease. If an aneurysm is present within an artery in the brain and bursts, this creates a subarachnoid hemorrhage, and a possibility that death may occur. Additionally, even with successful surgery, recovery takes several weeks and often requires a lengthy hospital stay.

In order to overcome some of these drawbacks, interventional methods and prostheses have been developed to provide an artificial structural support to the vessel region impacted by the aneurysm. The structural support must have an ability to maintain its integrity under blood pressure conditions and impact pressure within an aneurysmal sac and thus prevent or minimize a chance of rupture. U.S. Pat. No. 5,405,379 to Lane, discloses a self-expanding cylindrical tube which is intended to span an aneurysm and result in isolating the aneurysm from blood flow. While this type of stent-like device may reduce the risk of aneurysm rupture, the device does not promote healing within the aneurysm. Furthermore, the stent may increase a risk of thrombosis and embolism. Additionally, the wall thickness of the stent may undesirably reduce the fluid flow rate in a blood vessel. Stents typically are not used to treat aneurysms in a bend in an artery or in tortuous vessels such as in the brain because stents tend to straighten the vessel.

U.S. Pat. No. 5,354,295 to Guglielmi et al., describes a type of vasoclusion coil. Disadvantages of use of this type of coil are that the coil may compact, may migrate over time, and the coil does not optimize the patient's natural healing processes.

SUMMARY OF THE INVENTION

One embodiment of the present invention includes a method for treating an aneurysm. The method includes providing a biocompatible polymeric coil, sleeve or hollow string and transporting the string to an aneurysm. The aneurysm is then filled with the coil or string. The coil or string is cut when the aneurysm is substantially filled.

Another embodiment of the present invention includes a kit for treating an aneurysm. The kit includes a biocompatible polymeric string and a catheter for transporting the string to an aneurysm site. The kit also includes a mechanism for cutting the string. The kit optionally includes a biocompatible material for sealing the aneurysm and a balloon for shaping the biocompatible material at the aneurysm neck.

One other embodiment of the present invention includes a biocompatible string, sleeve or coil that comprises a stiff biocompatible core and an outer swellable material, concentrically positioned about the core. A water-soluble material concentrically contacts the outer swellable material and provides a time dependent swelling of the swellable material.

Another embodiment of the present invention includes a method for treating an aneurysm. The method includes providing a biocompatible hollow string or coil and positioning a wire within the hollow string or coil. The wire, string or coil are transported to an aneurysm. The wire is used to guide the string or coil into the aneurysm. The coil, sleeve or hollow string are cut when the aneurysm is substantially filled.

DETAILED DESCRIPTION

Figure 1:
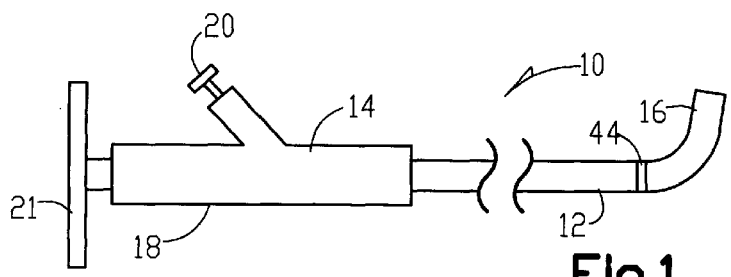
FIG. 1 is a side view of one embodiment of a catheter used for repairing an aneurysm with the method of the present invention.

One embodiment of the present invention includes a device for sealing and repairing an aneurysm. The device comprises a biocompatible polymeric string, such as is shown schematically at 26 in FIG. 2, that is positionable within an aneurysm sac 24 and that functions to fill and then to plug or seal the aneurysm. One biocompatible polymeric string embodiment comprises a hydrogel with drugs and other agents incorporated for healing the aneurysm. A polymeric string embodiment, illustrated in cross-section at 50 in FIG. 3, comprises a stiff hydrogel core 52 with a soft hydrogel foam portion 54 that concentrically surrounds the core 52. A gel 56 provides a concentric outer coating or encapsulation of the soft hydrogel foam 54.

The biocompatible polymeric string 26 is, in some embodiments, includes a radiopaque marker such as barium sulfate. The use of the marker enables a physician to determine proper placement and proper fill in the aneurysm sac 24.

The polymeric material 54 is, in one embodiment, a hydrogel foam portion which is swellable and has a swell ratio of 10:1–2:1. The hydrogel foam portion 54 is, for some embodiments, seeded with materials such as growth factors, integrins, cell attachment proteins, cells, and genes and gene products to speed cell overgrowth. The foam provides a desirable surface for rapid cell ingrowth. The hydrogel foam or other filler material is shapable at the aneurysm neck to form a smooth, closed surface at the aneurysm neck.

Figure 3:
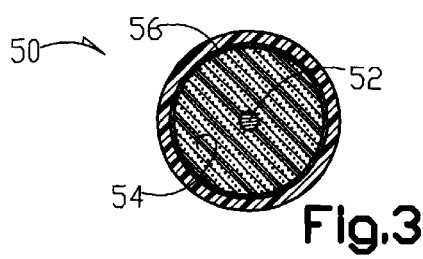
FIG. 3 is a radial cross-sectional view of one embodiment of the hydrogel sleeve, coil or string of the present invention.

Swellable materials for use in the present invention include acrylic based materials. For one embodiment, the core material is stiffer than the outer material, as shown in FIG. 3. In particular, FIG. 3 shows a cross-sectional area of a material 50 with the core hydrogel 52 and the surrounding foam hydrogel 54. An encapsulation layer 56 covers the foam hydrogel. This layer is gelatin-like and comprises a water dissolvable polymer. The layer, for some embodiments, has a time dependent rate of dissolution. The encapsulation layer is present to prevent premature swelling. The internal core hydrogel 52 may be stiffened as a consequence of an increased degree of crosslinkage as compared to the outer foam hydrogel 54, forming an outer jacket. In another embodiment, the core of the hydrogel string is a soft core metal wire.

The material is fabricated to form a long, continuous cylinder with a core surrounded by a jacket of soft, swellable hydrogel coated with a water soluble material, such as gelatin or other substance to prevent premature swelling. The material is placed into an aneurysm in a continuous fashion until angiographic filling is achieved. The material is then cut or detached. The encapsulation layer dissolves and allows the outer jacket material to swell to a much greater filling volumes than are possible with GDC coils.

While a hydrogel is described, it is understood that other biocompatible, swellable materials are suitable for use in the present invention. Other materials include cellulose acetate, ethylene vinyl alcohol copolymers, polyacrylonitrile, polyvinylacetate, cellulose acetate butyrate, nitrocellulose, copolymers of urethane/carbonate, copolymers of styrene/maleic acid, or mixtures thereof. In particular, it is contemplated that a hydrogel/polyurethane foam is usable in the sleeve, coil or string of the present invention.

Figure 6:
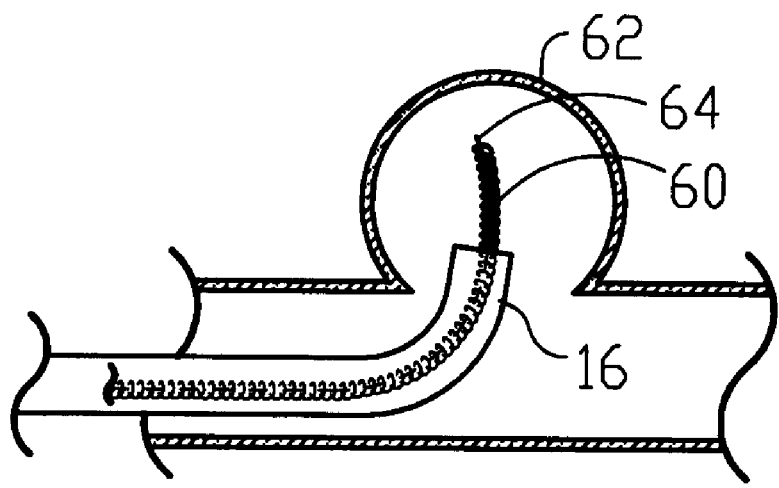
FIG. 6 is a side view of one hollow sleeve, coil, or string embodiment of the present invention positioned proximal to an aneurysm sac.
Figure 7:
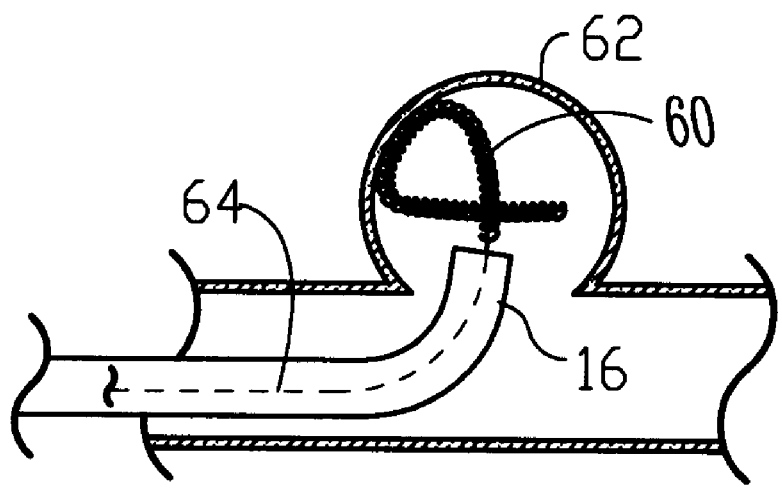
FIG. 7 is a side view of the hollow sleeve, coil, or string embodiment of FIG. 6 wherein the hollow sleeve, coil, or string is positioned within the aneurysm sac.

Another embodiment of the biocompatible sleeve, coil, or string of the present invention comprises a polymer-based, coil-like structure that is fabricated with soft biocompatible polymers such as ePTFE, urethanes, polyolefins, nylons and so forth, such as is shown at 60 in FIGS. 6 and 7. Sleeve or coil embodiments include hollow coils such as 60. String embodiments include solid strings and hollow strings. The sleeve, coil or string is fabricated by direct forming, machining, laser cutting, injection molding or coiling/braiding.

These string structures are also capable of fabrication with biodegradable materials such as PLA, PGA, PLGA, polyanhydrides and other similar biodegradable materials. A use of biodegradable materials provokes a wound healing response and concomitantly eliminates a mass effect of the filled aneurysm over time.

Figure 2:
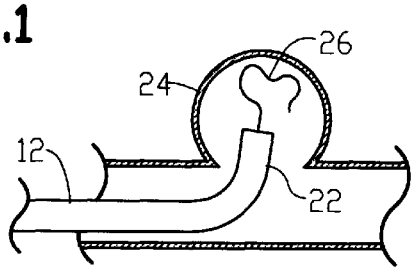
FIG. 2 is a schematic view of one embodiment of delivery of a hydrogel sleeve, coil or string to an aneurysm sac.

The biocompatible polymeric sleeve, coil or string 26 is deployed to an aneurysm sac 24 through a lumen, illustrated at 12 in FIG. 2, which is disposed within the aneurysm sac 24. The lumen 12 is a component of a catheter, such as is illustrated at 10 in FIG. 1. The stiff polymer core 52 is guided at 21 of the catheter. In another embodiment, the sleeve, coil or string is pre-fabricated and is guided at 20 or 21 of the catheter. In one other embodiment, a core wire, soft noble metal, gold, platinum, silver, etc. is used instead of the stiff polymer core to make the string.

In another embodiment, illustrated in FIGS. 6 and 7, a hollow sleeve or coil 60 or a, which is not shown, is transported to an aneurysm sac with a catheter 10. The hollow coil 60 or hollow string is delivered into an aneurysm sac 62 over a wire 64 which is positioned within the aneurysm sac. The coil 60 or 25 hollow string is delivered over the wire 64 and is positioned within the aneurysm 62 without requiring the catheter to enter the aneurysm.

Some embodiments of the polymer sleeve or coil 60 or string comprise a foam component. These embodiments also include cellular growth factors, genes, gene products and drugs within the foam or as a coating on the foam. These embodiments promote healing and repair of the aneurysm.

The sleeve, coil 60 or string is detachable either at the catheter tip or outside in small pushable sections. This embodiment does not require the catheter tip to enter the aneurysm, although the tip may enter the aneurysm. The wire essentially gains access and also functions as a rail to guide the polymer coil 60 or hollow string into the aneurysm. The wire 64 imparts strength and support sufficient to permit the coil or string to be pushed into the aneurysm without the material itself being required to have that support "built-in."

In another embodiment, the coil surface is modified to have an activated coating which causes the coils to bond, adhere or glue together. The modification may be biologic such as a fibrinogen activated surface or may be fabricated by standard chemical techniques. The surface could be made to be self adhesive and surface activatable, as well. This modification secondarily anchors the coils together prior to an in-growth of cells to complete aneurysmal healing.

The present invention also includes a method for sealing and repairing an aneurysm. The method comprises providing a swellable biocompatible polymeric string. Also provided is a catheter, such as is shown at 10 and FIG. 1, that comprises a lumen 12 having a proximal 14 and a distal end 16. The proximal end 14 comprises a manifold 18 with a port 24 for insertion of the biocompatible polymeric string. The biocompatible polymeric string is pushed through the lumen 12 to the distal end 16. The distal end 16, in one embodiment, terminates in a curved tip 22. The curved tip 22 is positionable within an aneurysm sac 24 as is shown in FIG. 2.

Figure 4:
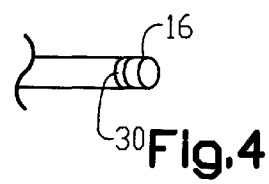
FIG. 4 is a side view of a distal tip of a catheter used on the method of the present invention, the tip comprising a mechanism for heating the hydrogel string to terminate the string.
Figure 5A:
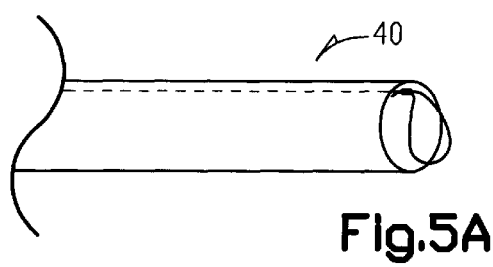
FIGS. 5a and 5c are a side view of one mechanical cutter mechanism for cutting the hydrogel string.
Figure 5B:
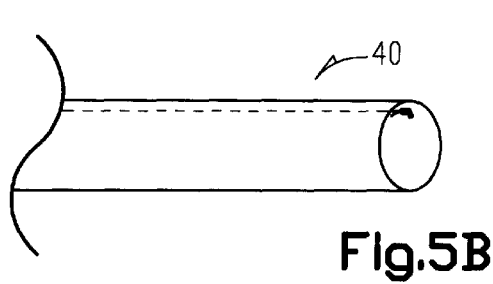
FIGS. 5b and 5d are a side view of the mechanical cutter mechanism of FIG. 5a in a closed position.
Figure 5C:
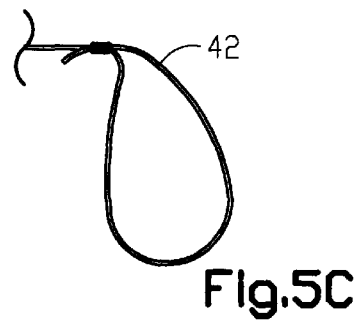
Figure 5D:
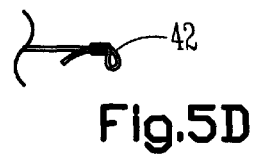

The biocompatible polymeric string may be detached with a heater, such as is shown at 30 in FIG. 4 or cut with a mechanical cutter, shown at 40 in FIGS. 5a and 5b, located at the distal end 16 of the lumen. In the embodiment in FIG. 4, the string 26 is detached with a heater which may be an electrical-based heater or a laser 30.

In another embodiment illustrated at 40 in FIGS. 5A and 5B, the hydrogel string 26 is cut with a mechanical loop cutter 42. The loop cutter 42 may 30 be manipulated in order to decrease the loop in diameter and cut through the polymer material 26.

The lumen 12 of catheter 10 has a generally circular cross-sectional configuration with an external diameter in a range of about 0.01 to 0.5 inches for cerebral vascular applications. The lumen 12 has sufficient structural integrity to permit the catheter 10 to be advanced to distal arterial locations without buckling or undesirable bending of the lumen 12.

In one embodiment, the distal tip 16 of the lumen includes a marker band 44. The marker band is radiopaque and may be made from materials such as platinum, gold, tungsten, rhenium alloy and alloys of these materials.

It will be understood that the embodiments of the present invention which have been described as illustrative of some of the applications of the principles of the present invention. Various modifications may be made by those skilled in the art without departing from the spirit and scope of the invention.

What is claimed is:

1. A method for treating an aneurysm, comprising:
   providing a biocompatible, swellable, polymeric material;
   shaping the biocompatible, swellable, polymeric material to form a long, continuous cylinder free of a predesignated cutting region;
   transporting the shaped, biocompatible, swellable, polymeric material to an aneurysm;
   filling the aneurysm with the shaped, biocompatable, swellable, polymeric material; and
   cutting said long, continuous cylinder.

2. The method of claim 1 and further comprising forming a sleeve that overlays the biocompatable, swellable, polymeric material, the sleeve comprising a swellable hydrogel.

3. The method of claim 2 and further comprising coating the swellable, hydrogel with an encapsulation layer.

4. The method of claim 1 and further comprising adding cell growth factors to the biocompatible polymeric material.

5. The method of claim 1 wherein the biocompatible polymeric material comprises a hydrogel.

6. The method of claim 1 and further comprising providing an aneurysm filler.

7. The method of claim 5 and further comprising shaping the filler to form a seal.

8. The method of claim 1 wherein the long, continuous cylinder is cut anywhere along the length of the long cylinder with a loop cutter.

9. The method of claim 1 wherein the long, continuous cylinder is cut anywhere along the length of the long cylinder with a laser cutter.

10. The method of claim 1 wherein the long, continuous cylinder is cut with heat.

11. The method of claim 1 wherein the polymeric material comprises a hydrogel.

12. The method of claim 1 wherein the polymeric material comprises one or more of cellulose acetate, ethylene vinyl alcohol copolymers, polyacrylonitrile, polyvinylacetate, cellulose acetate butyrate, nitrocellulose, copolymers of urethane/carbonate, copolymers of styrene/maleic acid, and mixtures thereof.

13. The method of claim 1 wherein the long, continuous cylinder has a string shape.

14. The method of claim 13 wherein the string is fabricated from a soft, biocompatible material.

15. The method of claim 13 wherein the string is fabricated from a biodegradable material.

16. The method of claim 1 wherein the long, continuous cylinder has a sleeve shape.

17. The method of claim 1 wherein the long, continuous cylinder has a coil shape.

* * * * *